US010786292B2

(12) United States Patent
Singh et al.

(10) Patent No.: US 10,786,292 B2
(45) Date of Patent: Sep. 29, 2020

(54) PATIENT-SPECIFIC BRIDGING PLATES

(71) Applicant: Stryker European Holdings I, LLC, Kalamazoo, MI (US)

(72) Inventors: Manoj Kumar Singh, Mahwah, NJ (US); Boon Quah, Nyack, NY (US); Bradley Michael Lamm, North Palm Beach, FL (US)

(*) Notice: Subject to any disclaimer, the term of this patent is extended or adjusted under 35 U.S.C. 154(b) by 195 days.

(21) Appl. No.: 16/011,123

(22) Filed: Jun. 18, 2018

(65) Prior Publication Data
US 2018/0360477 A1 Dec. 20, 2018

Related U.S. Application Data

(60) Provisional application No. 62/520,957, filed on Jun. 16, 2017.

(51) Int. Cl.
*A61B 17/80* (2006.01)
(52) U.S. Cl.
CPC ...... *A61B 17/8061* (2013.01); *A61B 17/8047* (2013.01); *A61B 17/8057* (2013.01); *A61B 17/8014* (2013.01)
(58) Field of Classification Search
CPC . A61B 17/80; A61B 17/8004; A61B 17/8014; A61B 17/8033; A61B 17/8047; A61B 17/8052; A61B 17/8057; A61B 17/8061
See application file for complete search history.

(56) References Cited

U.S. PATENT DOCUMENTS

| 2,825,329 | A | * | 3/1958 | Caesar | A61B 17/80 606/71 |
| 3,709,218 | A | | 1/1973 | Halloran | |
| 3,900,025 | A | * | 8/1975 | Barnes, Jr. | A61B 17/8004 606/71 |
| 4,235,428 | A | | 11/1980 | Davis | |
| 4,719,907 | A | | 1/1988 | Banko et al. | |
| 4,969,886 | A | | 11/1990 | Cziffer et al. | |

(Continued)

FOREIGN PATENT DOCUMENTS

WO 2016112469 A1 7/2016

OTHER PUBLICATIONS

Partial European Search Report and Written Opinion for EP Application No. 18178063.6, dated Nov. 19, 2018.

(Continued)

*Primary Examiner* — Eric S Gibson
(74) *Attorney, Agent, or Firm* — Lerner, David, Littenberg, Krumholz & Mentlik, LLP

(57) ABSTRACT

Disclosed herein are a bone plating system and a method for utilizing the same. The bone plating system may include first and second bone plates in contact with respective first and second bones, a cross-connector, a cutting guide and a targeter device. The cross-connector may have a first end and an opposite second extending along a longitudinal axis from the first bone plate to the second bone plate. The cutting guide may have an elongate body placed on one of the first or second bones. The targeter device may have a drill guide to align the cross-connector with the first and second bone plates. A method for fixing the bone plating system to the first and second bone may include using the targeter device.

17 Claims, 14 Drawing Sheets

(56) References Cited

U.S. PATENT DOCUMENTS

| | | |
|---|---|---|
| 5,529,075 A | 6/1996 | Clark |
| 5,916,219 A | 6/1999 | Matsuno et al. |
| 5,921,986 A | 7/1999 | Bonutti |
| 6,139,550 A | 10/2000 | Michelson |
| 6,183,477 B1 | 2/2001 | Pepper |
| 6,221,073 B1 | 4/2001 | Weiss et al. |
| 6,287,307 B1 | 9/2001 | Abboudi |
| 6,932,818 B2 | 8/2005 | Behrens |
| 7,090,676 B2 | 8/2006 | Huebner et al. |
| 7,147,640 B2 | 12/2006 | Huebner et al. |
| 7,153,309 B2 | 12/2006 | Huebner et al. |
| 7,189,237 B2 | 3/2007 | Huebner |
| 7,198,628 B2 | 4/2007 | Ondrla et al. |
| 7,235,079 B2 | 6/2007 | Jensen et al. |
| 7,326,212 B2 | 2/2008 | Huebner |
| 7,347,861 B2 | 3/2008 | Johnstone |
| 7,410,489 B2 | 8/2008 | Dakin et al. |
| 7,537,596 B2 | 5/2009 | Jensen |
| 7,537,603 B2 | 5/2009 | Huebner et al. |
| 7,537,604 B2 | 5/2009 | Huebner |
| 7,578,825 B2 | 8/2009 | Huebner |
| 7,621,920 B2 | 11/2009 | Claypool et al. |
| 7,635,365 B2 | 12/2009 | Ellis et al. |
| 7,648,508 B2 | 1/2010 | Lutz et al. |
| 7,658,741 B2 | 2/2010 | Claypool et al. |
| 7,704,251 B2 | 4/2010 | Huebner et al. |
| 7,717,945 B2 | 5/2010 | Jensen et al. |
| 7,794,467 B2 | 9/2010 | McGinley et al. |
| 7,837,717 B2 | 11/2010 | Deffenbaugh et al. |
| 7,857,836 B2 | 12/2010 | Huebner et al. |
| 7,914,532 B2 | 3/2011 | Shaver et al. |
| 7,927,332 B2 | 4/2011 | Huebner et al. |
| 7,955,388 B2 | 6/2011 | Jensen et al. |
| 8,043,297 B2 | 10/2011 | Grady, Jr. et al. |
| 8,187,308 B2 | 5/2012 | Mullaney et al. |
| 8,231,627 B2 | 7/2012 | Huebner et al. |
| 8,231,662 B2 | 7/2012 | Huebner |
| 8,262,706 B2 | 9/2012 | Olms et al. |
| 8,313,492 B2 | 11/2012 | Wong et al. |
| 8,328,809 B2 | 12/2012 | Wenk et al. |
| 8,372,078 B2 | 2/2013 | Collazo |
| 8,398,678 B2 | 3/2013 | Baker et al. |
| 8,398,717 B2 | 3/2013 | Kleinman |
| 8,403,966 B2 | 3/2013 | Ralph et al. |
| 8,425,574 B2 | 4/2013 | Huebner et al. |
| 8,425,575 B2 | 4/2013 | Huebner et al. |
| 8,475,504 B2 | 7/2013 | Gillard et al. |
| 8,500,745 B2 | 8/2013 | Kuenzi et al. |
| 8,506,597 B2 | 8/2013 | Kaiser et al. |
| 8,523,919 B2 | 9/2013 | Huebner et al. |
| 8,579,900 B2 | 11/2013 | Hsu |
| 8,585,744 B2 | 11/2013 | Duggal et al. |
| 8,628,531 B2 | 1/2014 | Ritchey et al. |
| 8,652,142 B2 | 2/2014 | Geissler |
| 8,685,030 B2 | 4/2014 | Gotte et al. |
| 8,764,763 B2 | 7/2014 | Wong et al. |
| 8,821,580 B2* | 9/2014 | DaSilva ............... A61B 17/683 606/297 |
| 8,886,496 B2 | 11/2014 | Graumann |
| 9,060,790 B2 | 6/2015 | Wayne et al. |
| 9,186,163 B2 | 11/2015 | Cleveland et al. |
| 9,241,744 B2 | 1/2016 | Blake et al. |
| 9,308,033 B2 | 4/2016 | Huebner et al. |
| 9,320,553 B2* | 4/2016 | Katrana ............... A61B 17/8061 |
| 9,339,279 B2 | 5/2016 | Dubois et al. |
| 9,370,386 B2 | 6/2016 | Galm et al. |
| 9,402,636 B2 | 8/2016 | Collazo |
| 9,414,871 B2 | 8/2016 | Huebner et al. |
| 9,414,873 B2 | 8/2016 | Graham et al. |
| 9,474,539 B2 | 10/2016 | Catanzarite et al. |
| 2003/0135212 A1* | 7/2003 | Y. Chow ............... A61B 17/72 606/64 |
| 2004/0116930 A1 | 6/2004 | O'Driscoll et al. |
| 2005/0216010 A1 | 9/2005 | Michelson |
| 2005/0234472 A1 | 10/2005 | Huebner |
| 2005/0273112 A1 | 12/2005 | McNamara |
| 2006/0015102 A1 | 1/2006 | Toullec et al. |
| 2006/0195198 A1 | 8/2006 | James |
| 2006/0241592 A1 | 10/2006 | Myerson et al. |
| 2006/0285931 A1 | 12/2006 | Dean |
| 2007/0225715 A1 | 9/2007 | Deffenbaugh et al. |
| 2007/0276386 A1 | 11/2007 | Gerlach et al. |
| 2008/0027434 A1 | 1/2008 | Zucherman et al. |
| 2008/0119895 A1 | 5/2008 | Manceau |
| 2008/0183218 A1* | 7/2008 | Mueller ............... A61B 17/7068 606/280 |
| 2009/0029320 A1 | 1/2009 | Auderset et al. |
| 2009/0228049 A1 | 9/2009 | Park |
| 2009/0254126 A1 | 10/2009 | Orbay et al. |
| 2009/0306675 A1 | 12/2009 | Wong et al. |
| 2009/0312802 A1* | 12/2009 | DaSilva ............... A61B 17/683 606/304 |
| 2009/0326591 A1 | 12/2009 | Spencer, Jr. |
| 2010/0318086 A1* | 12/2010 | Winemaker ........... A61B 17/683 606/70 |
| 2011/0009866 A1 | 1/2011 | Johnson et al. |
| 2011/0213376 A1 | 9/2011 | Maxson et al. |
| 2011/0245930 A1 | 10/2011 | Alley et al. |
| 2012/0130434 A1 | 5/2012 | Stemniski |
| 2012/0130686 A1 | 5/2012 | Graumann |
| 2013/0018424 A1* | 1/2013 | Subik ............... A61B 17/1728 606/281 |
| 2013/0211463 A1 | 8/2013 | Mizuno et al. |
| 2013/0226248 A1 | 8/2013 | Hatch et al. |
| 2013/0245602 A1 | 9/2013 | Sweeney |
| 2013/0296872 A1 | 11/2013 | Davison et al. |
| 2014/0058466 A1 | 2/2014 | Keppler et al. |
| 2014/0107781 A1 | 4/2014 | Bagga et al. |
| 2014/0180341 A1 | 6/2014 | Kang et al. |
| 2014/0336658 A1 | 11/2014 | Luna et al. |
| 2015/0032168 A1 | 1/2015 | Orsak et al. |
| 2015/0045837 A1 | 2/2015 | Parekh et al. |
| 2015/0051650 A1 | 2/2015 | Verstreken et al. |
| 2015/0051876 A1 | 2/2015 | Rueber et al. |
| 2015/0057665 A1 | 2/2015 | Neal et al. |
| 2015/0080717 A1 | 3/2015 | Ferko |
| 2015/0112343 A1 | 4/2015 | Medoff et al. |
| 2015/0119987 A1 | 4/2015 | Davignon et al. |
| 2015/0223824 A1 | 8/2015 | Mebarak |
| 2015/0257899 A1 | 9/2015 | Luna et al. |
| 2015/0272598 A1 | 10/2015 | Dubois et al. |
| 2015/0305752 A1 | 10/2015 | Eash |
| 2015/0366594 A1 | 12/2015 | Berghs et al. |
| 2016/0022336 A1 | 1/2016 | Bateman |
| 2016/0030064 A1* | 2/2016 | Dacosta ............... A61B 17/1717 606/64 |
| 2016/0038186 A1 | 2/2016 | Herzog et al. |
| 2016/0051298 A1 | 2/2016 | Malinin |
| 2016/0235445 A1 | 8/2016 | Katrana et al. |
| 2016/0287335 A1 | 10/2016 | Goto |
| 2017/0027628 A1 | 2/2017 | Kim et al. |
| 2017/0119405 A1 | 5/2017 | Triplett et al. |
| 2018/0289380 A1 | 10/2018 | Mauldin et al. |
| 2018/0360477 A1* | 12/2018 | Singh ............... A61B 17/683 |

OTHER PUBLICATIONS

Extended European Search Report and Written Opinion for EP Application No. 18178063.6, dated Apr. 8, 2019.

Dobbe, et al., "Patient-Tailored Plate for Bone Fixation and Accurate 3D Positioning in Corrective Osteotomy", vol. 51, No. 1-2, Medical & Biological Engineering & Computing, Feb. 2013, pp. 19-27.

Extended European Search Report and Written Opinion for EP Application No. 18165822.0, dated Sep. 5, 2018.

* cited by examiner

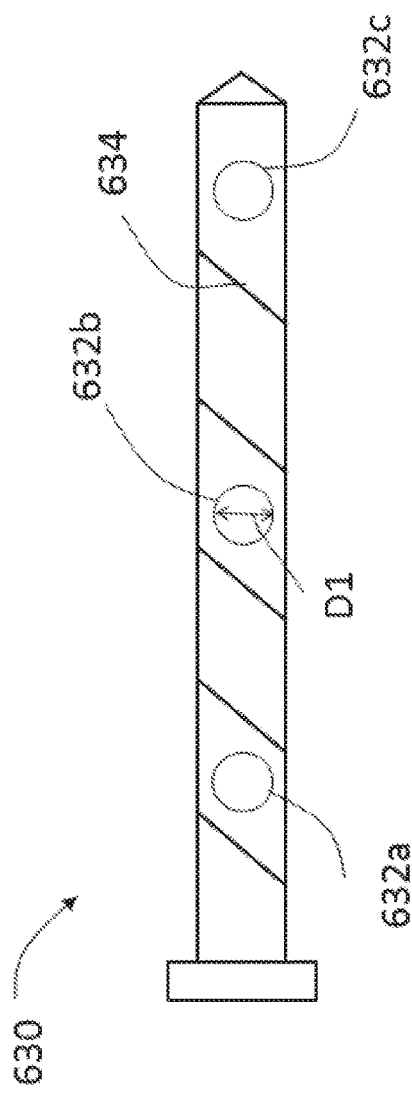
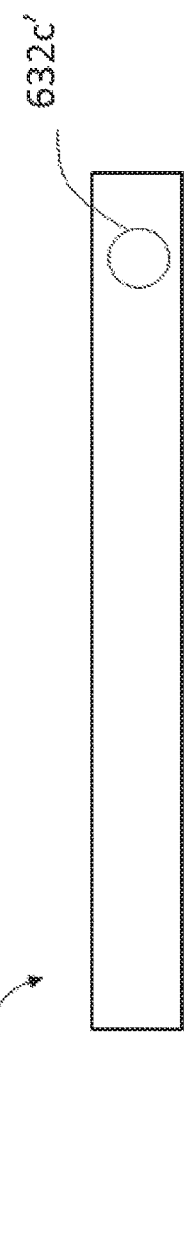
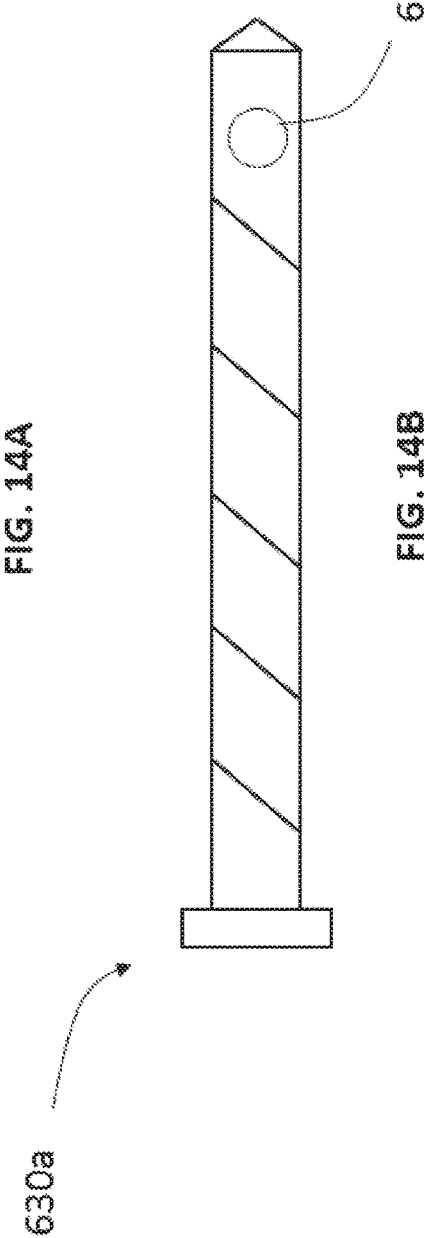
FIG. 13
FIG. 14A
FIG. 14B

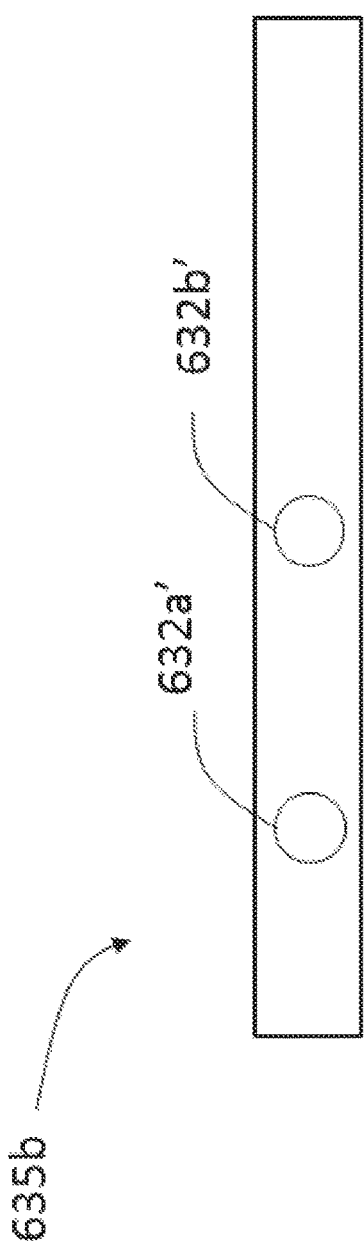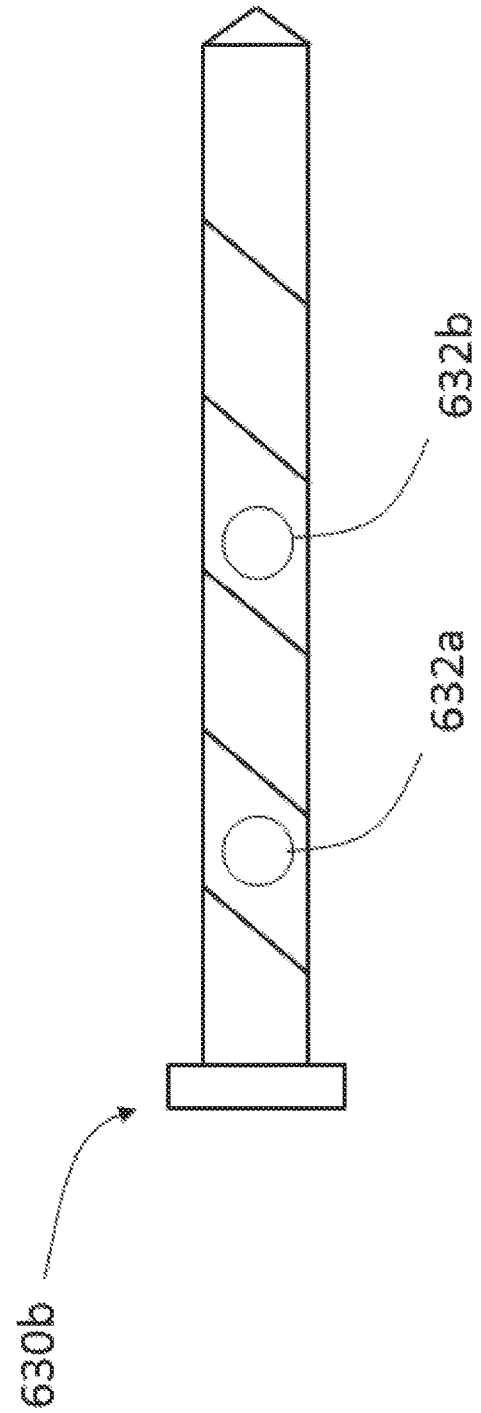

PATIENT-SPECIFIC BRIDGING PLATES

CROSS-REFERENCE TO RELATED APPLICATION

The present application claims the benefit of the filing date of U.S. Provisional Patent Application No. 62/520,957, filed on Jun. 16, 2017, the disclosure of which is hereby incorporated by reference.

FIELD OF THE INVENTION

The present invention generally relates to a bone plating system and a method for attaching bone plating assembly, and in particular a bridging bone plate system and a method of implanting a bridging bone plate assembly.

BACKGROUND OF THE INVENTION

Bone plates are generally used for securing bone fragments or multiple bones in a fixed position to facilitate bone fusion and healing. For example, a bone fracture may be treated by affixing a bone plate to the fracture area, whereby the bone plate reduces the fracture gap and provides support for the fractured bone to heal. Bone plates perform similar functions in treating bone deformities.

Bone plates are typically attached to bone using bone screws. Fixation by bone screws may be insufficient in some instances, especially when the bone plate is attached across multiple bones. In some cases, the location and number of screw holes on the bone plate is insufficient for proper plate fixation. For example, if the location of a screw hole corresponds to a weak bone area in a patient with osteoporosis, then the bone plate may not be properly secured and the one or more bone portions may not be properly aligned.

Treating Charcot or midfoot deformities, for example, may require multiple bone plates with multiple bone screws. Such constructs may increase the risk of one or more of bone plates being inadequately secured to the bones. When multiple bone plates are used, a connecting element such as a connecting rod or a connecting bolt may be used to attach both bone plates. Connecting elements bridging two bone plates generally provide compressive force and may improve the bone plate to bone fixation for both bone plates and simultaneously improve stability of bone plate assembly, i.e., bone plates and connecting element.

Attaching two bone plates with a connecting element may be challenging because proper alignment between the two bone plates should be maintained to ensure that the connecting element is properly secured to both bone plates, while simultaneously ensuring proper bone plate to bone contact is maintained. Further, this alignment must be properly identified and maintained during the surgical procedure to allow for proper bone preparation.

Therefore, there exists a need for improved bone plating systems and methods for implanting the same.

BRIEF SUMMARY OF THE INVENTION

Disclosed herein are bone plating systems and methods for implanting the same.

In a first aspect of the present invention, a bone plating system is provided. The bone plating system may have first and second bone plates, a cross-connector, a cutting guide and a targeter device. The first and second bone plates may be in contact with respective first and second bones. The cross-connector may have a first end and an opposite second end. The cross-connector may extend along a longitudinal axis from the first bone plate to the second bone plate. The cutting guide may have an elongate body with a bone contacting surface that may be configured to be placed on one of the first and second bones to define the longitudinal axis. The targeter device may have a drill guide to align the cross-connector with the first and second bone plates along the longitudinal axis.

In accordance with the first aspect, the bone plating system may further include an insert housed within one of the first and second bone plates. The second end of the cross-connector may engage with the insert to secure the cross-connector about the longitudinal axis. One of the first and second bone plates with the insert may be movable about at least one axis. The one axis may extend through the bone plate when the bone plate is secured to the cross-connector. The insert may be any of a ball joint nut, pivot nut and flexible nut.

In other aspects, the cross-connector may include a first threaded portion which may be used to engage with one of the first and second bone plates. The cross-connector may include a second threaded portion which may be used to engage with the other of the first and second bone plates. The first and second bone plates may have corresponding threading to engage with the first and second threated portions of the cross-connector.

The second bone plate may include an outer surface which may have a collar portion extending outwardly from the outer surface. The second end of the cross-connector may be at least partially disposed within the collar when the cross-connector is secured to the first and second bone plates.

The second bone plate may include a bone contacting surface which may include a collar portion extending outwardly from the bone contacting surface. The second of the cross-connector may be at least partially disposed within the collar when the cross-connector is secured to the first and second bone plates.

The first and second bone plates may each have at least one fixation hole. The fixation hole may be configured to receive a fixation element to secure the first and second bone plates to the respective first and second bones. The at least one fixation hole may be a compression slot.

In still other aspects, the first bone plate may contact at least one of a metatarsal bone, a cuneiform bone, a navicular bone and a talus bone. The second bone plate may contact at least one of a cuboid bone and a calcaneus bone.

The first bone and second bone plates may be preoperatively planned to match an outer surface of the respective first and second bones and to secure the cross-connector along the longitudinal axis.

The cutting guide may have a slot extending through the elongate body. The slot may have a central axis collinear with the longitudinal axis.

The targeter device may include a frame with a first arm and a second arm. A through hole through each of the first and second arms may define a targeter axis extending from the first arm to the second arm. The targeter axis may be collinear with the longitudinal axis when the first and second arms are engaged with the respective first and second bones. At least one of the first arm and the second arm may be a spring loaded retractable arm such that the targeter device may be retractable along the targeter axis. The first and second spring loaded retractable arms may couple the targeter device to the first and second bone plates such that the targeter axis may be collinear with the longitudinal axis. The longitudinal axis may be generally transverse to the first and second bone plates.

In accordance to other aspects, at least a third bone may be disposed between the first and second bones. The cross-connector may extend through the third bone to secure the first, second and third bones with the first and second bone plates.

In accordance to other aspects, the cross-connector may have a channel in fluid communication with one or more outlets disposed on an outer surface of the cross-connector. The channel may have an inlet to receive a biologic fluid. The channel may be internal to cross-connector such that it forms a cylinder or tube-like structure having an inlet and outlet.

A second aspect of the present invention is a method of fixing a bone plating system to at least a first bone and a second bone with at least a third bone disposed between the first and second bones. A method in accordance with this aspect of the invention may include the steps of placing a bone contacting surface of a cutting guide on the first bone surface, drilling a first hole through a slot in the cutting guide, placing a first bone plate on the first bone and a second bone plate on the second bone, placing a first arm of a targeter device on the first bone plate and a second arm of the targeter device on the second bone plate, drilling a second hole through the first hole using the first and second arms of the targeter device and securing a cross-connector through the second hole. The first and second bone plates may secure the first bone, second bone and third bone. The cutting guide may have an elongate body. The drilled hole through the slot in the cutting guide may extend through the first and second bones.

In a third aspect of the present invention, a bone screw is provided. A bone screw according to this third aspect may include a bore and an insert configured to be received within the bore. The bore may be in fluid communication with one or more outlets. The one or more outlets may be disposed on an exterior surface of the bone screw. The insert may have a channel with one or more openings in fluid communication with the channel. The one or more openings may be disposed on an outer surface of the insert. When the insert is placed in the bore, at least one outlet may be in fluid communication with at least one opening. The channel may include a biologic fluid. The bore and channel may be internal to bone screw and cross-connector respectively such that each forms a cylinder or tube-like structure having an inlet and outlet.

BRIEF DESCRIPTION OF THE DRAWINGS

A more complete appreciation of the subject matter of the present invention and the various advantages thereof can be realized by reference to the following detailed descriptions, in which reference is made to the accompanying drawings:

FIG. 13 is side view of a bone screw according to another embodiment of the present invention;

FIG. 14A is a side view of a first insert for the bone screw of FIG. 13;

FIG. 14B is side view of the bone screw of FIG. 13 in conjunction with the first insert, and FIG. 15A is a side view of a second insert for the bone screw of FIG. 13, and FIG. 15B is a side view of the bone screw of FIG. 13 in conjunction with the second insert.

DETAILED DESCRIPTION

In describing preferred embodiments of the disclosure, reference will be made to directional nomenclature used in describing the human body. It is noted that this nomenclature is used only for convenience and that it is not intended to be limiting with respect to the scope of the invention.

As used herein, when referring to bones or other parts of the body, the term "anterior" means toward the front part or the face and the term "posterior" means toward the back of the body. The term "medial" means toward the midline of the body and the term "lateral" means away from the midline of the body. The term "superior" means closer to the heart and the term "inferior" means more distant from the heart.

Figure 1:
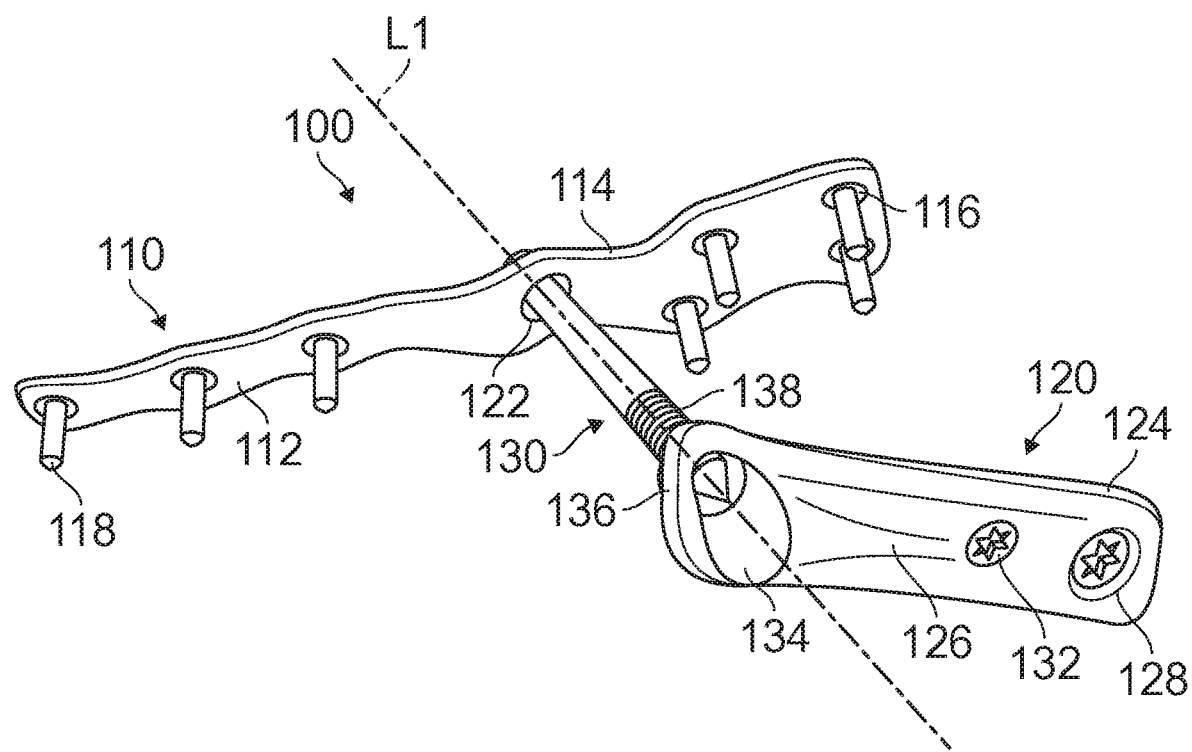
FIG. 1 is a perspective view of a bone plating assembly according to one embodiment of the present invention.

Referring to FIG. 1, there is shown a perspective view of a bone plating assembly 100. Bone plating assembly 100 includes a medial bone plate 110, a lateral bone plate 120 and a cross-connector 130 joining the bone plates. Medial bone plate 110 has a generally rigid elongate body with a first bone contacting surface 112 and an opposite first surface 114. First bone contacting surface 112 is configured to match bone profile. A plurality of screw holes 116 configured to receive bone screws 118 are located throughout medial bone plate 110. A centrally located first fixation hole 122 allows cross-connector 130 to be coupled with medial bone plate 110. Whereas fixation hole 122 is centrally located on medial bone 110 in this embodiment, other embodiments may have fixation hole 122 located at different locations on medial bone plate 110. Central positioning of first fixation hole 122 allows for improved fixation between cross-connector 130 and medial bone plate 110, whereby stress induced by the cross-connector on medial bone plate 110 is evenly distributed across the bone plate.

Lateral bone plate 120 is also a rigid elongate plate with a second bone contacting surface 124 and an opposite second surface 126. Similar to the medial bone plate 110, second bone contacting surface 124 is configured to match profile of bone surface(s) on which lateral plate 120 is implanted. A plurality of screw holes 128 configured to accept bone screws 132 are located at one end of medial bone plate 120. An opposite end of medial bone plate 120 includes a second fixation hole 134 to engage with cross-connector 130. Second fixation hole 134 is disposed within a collar 136. Cross-connector 130 includes a threaded portion 138 to engage with second fixation hole 134 of medial bone plate 120. As best seen in FIG. 1, a central axis L1 of cross-connector 130 is aligned with first fixation hole 122 and second fixation hole 134.

Figure 2:
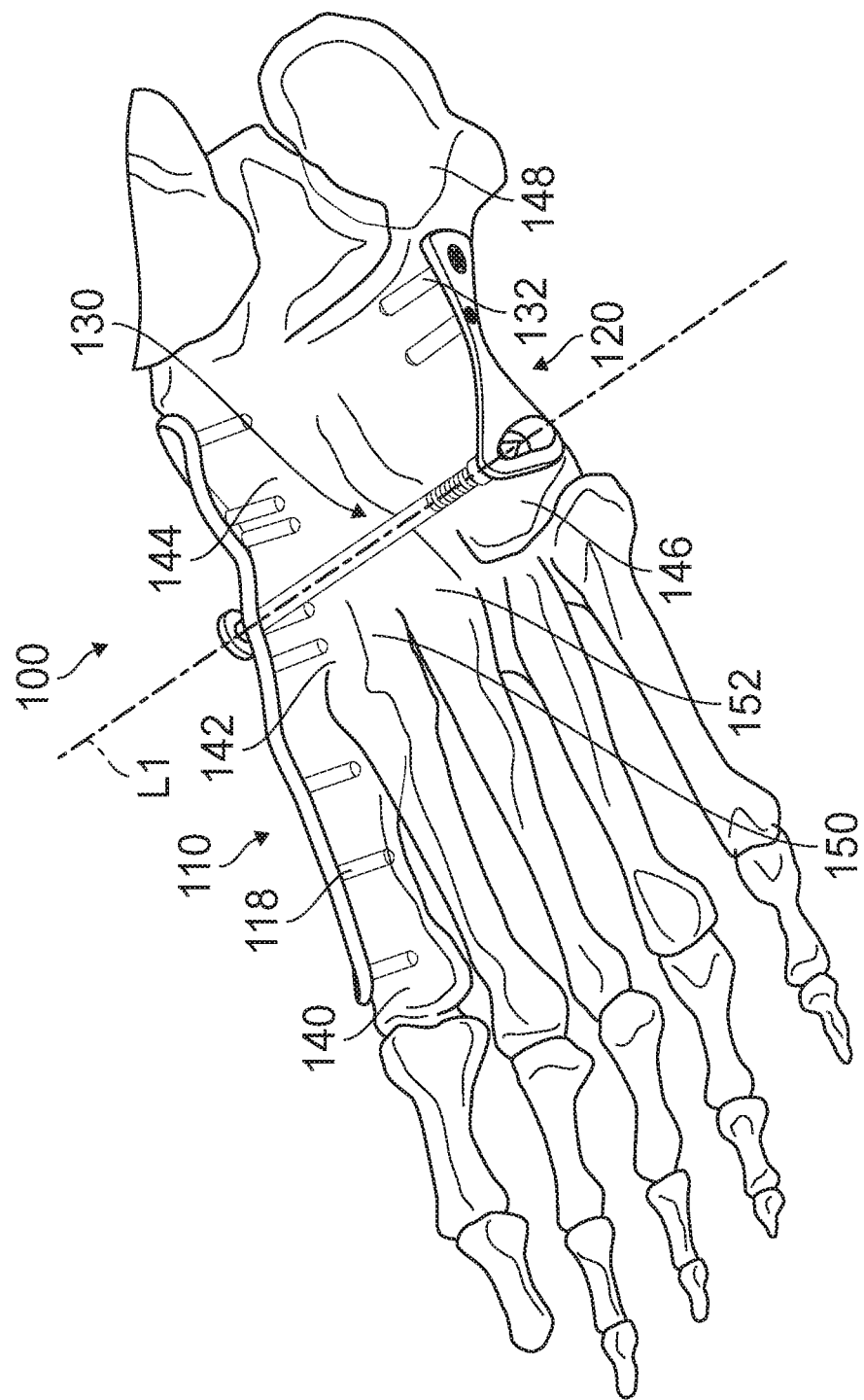
FIG. 2 is a another perspective view of the bone plating assembly of FIG. 1.

FIG. 2 is another perspective view of bone plating assembly 100 implanted on a human foot. Medial bone plate 110 is attached by bone screws 118 to a metatarsal bone 140, a medial cuneiform bone 142, and a navicular bone 144 and rigidly secures these bones. Similarly, lateral bone plate 120 is attached by bone screws 132 and rigidly secures a cuboid bone 146 and a calcaneus bone 148. Cross-connector 130 passes through medial cuneiform bone 142, an intermediate cuneiform bone 150, a lateral cuneiform bone 152 and cuboid bone 146. As shown in the present embodiment, there are at least two other bone, i.e., medial and intermediate cuneiform bones 150, 152, between medial bone plate 110 and lateral bone plate 120. When fully implanted, bone plate assembly 100 ensures that in addition to bone plates 110, 120 rigidly securing bones 140, 142, 144, 146, 148, the cross-connector 130 coupling the bone plates applies a compressive force across bones 150,152. While bone screws 118, 132 secure bone plates 110, 120 respectively, the cross-connector compressive force reinforces the bone plate to bone attachment and provides greater fixation between bone plates and bones as compared to fixation achieved with only bone screws.

Figure 3B:
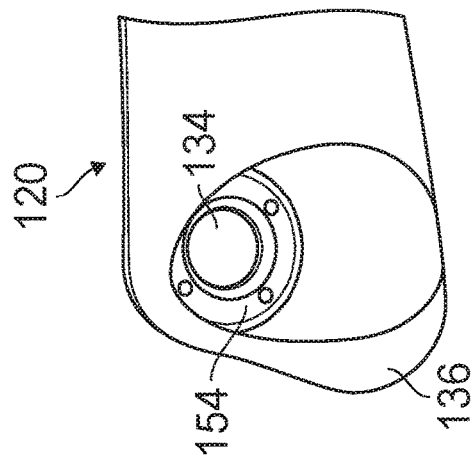
FIGS. 3B and 3C are details of a ball joint nut of the lateral bone plate of FIG. 3A.
Figure 3C:
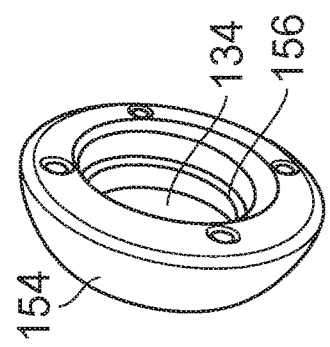
Figure 3A:
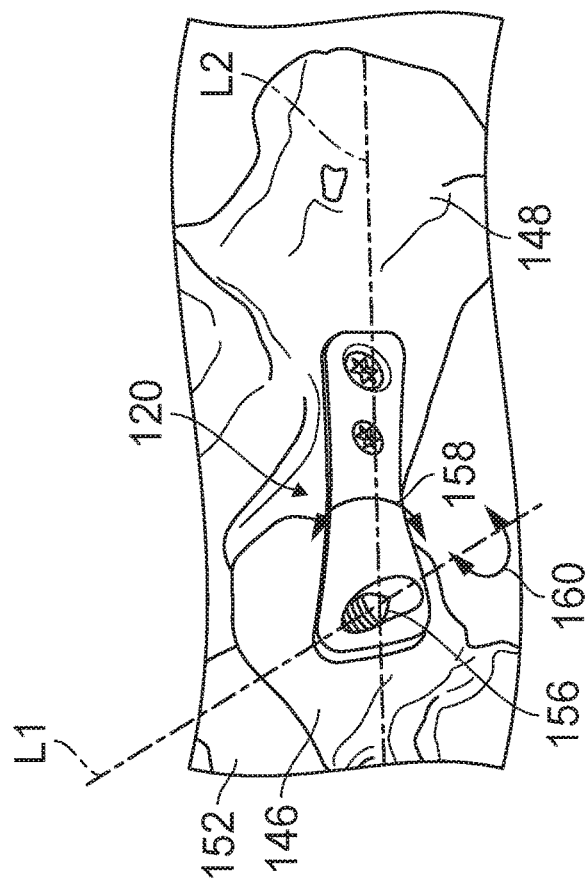
FIG. 3A is a perspective view of a lateral bone plate of the bone plating assembly of FIG. 1.

Referring now to FIG. 3A, there is shown a perspective view of lateral bone plate 120 implanted on cuboid bone 146 and calcaneus bone 148. A longitudinal axis L2 extending through the center of lateral bone plat 120 intersects with central axis L1 of cross-connector 130. As best shown in FIGS. 3B and 3C, second fixation hole 134 includes a ball nut joint 154 housed in second fixation hole 134. Threaded portion 138 of cross-connector 130 is configured to engage with a threaded portion 156 of ball nut joint 154. Ball nut joint 154 allows lateral bone plate 120 to pivot about an intersection 156 of longitudinal axis L2 and central axis L1 when lateral bone plate 120 is threadingly secured with cross-connector 130. As shown in FIG. 3A, ball joint nut 154 allows lateral bone plate 120 to pivot about intersection 156 along axis L1 and axis L2 indicated by rotation arrows 158 and 160 respectively. Pivoting capability allows for greater flexibility in attaching lateral bone plate 120 to cuboid bone 146 and calcaneus bone 148, whereby lateral bone plate 120 may be adjusted and positioned as desired over bones 146, 148 even after being firmly secured to cross-connector 130. While a ball nut joint providing multi-axial freedom for lateral bone plate 120 is shown in this embodiment, other embodiments may have other joint mechanisms that may allow freedom only along certain axes.

Figure 4:
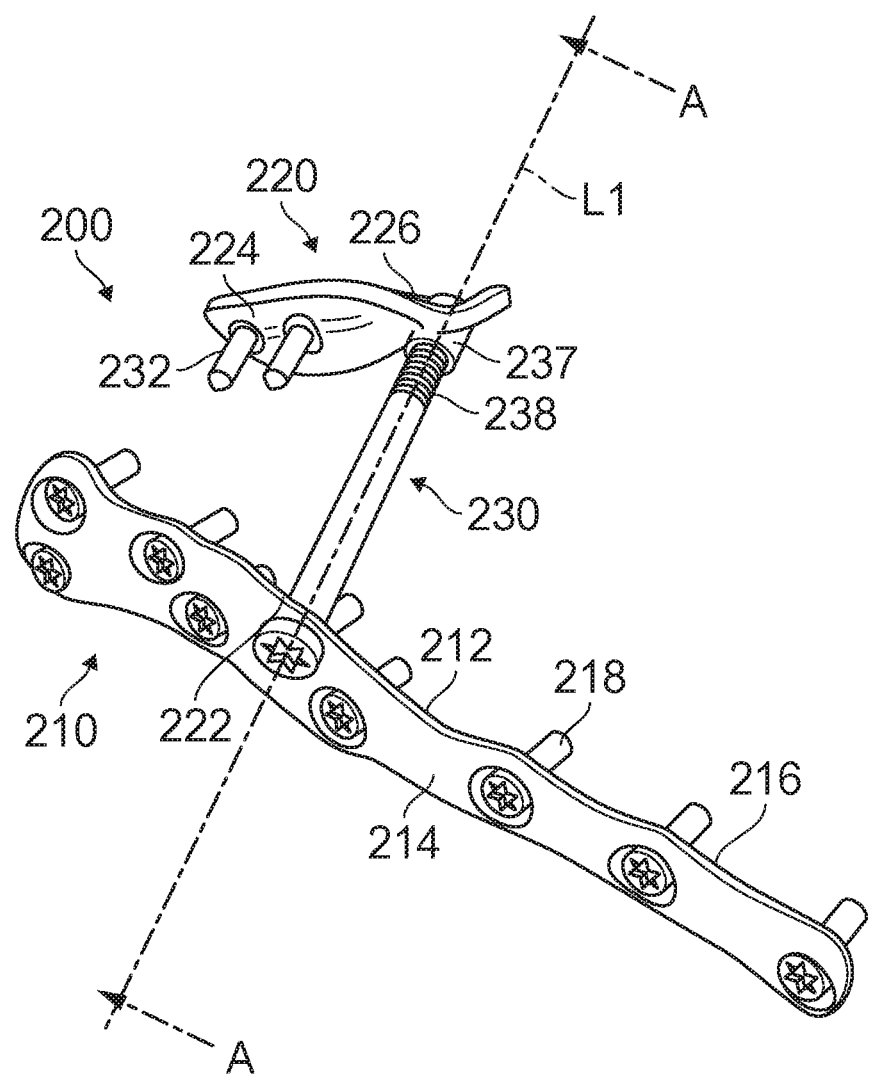
FIG. 4 is a perspective view of a bone plating assembly according to another embodiment of the present invention.
Figure 5:
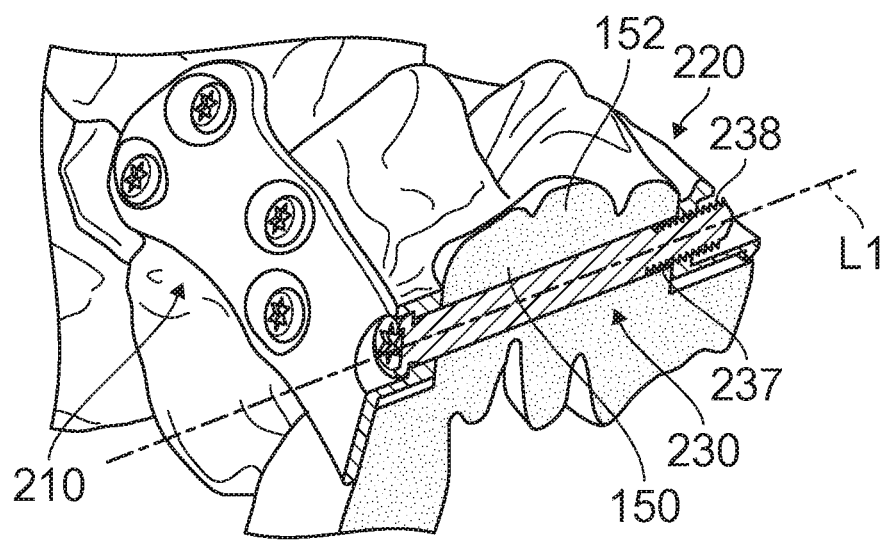
FIG. 5 is a cross-sectional view along line A-A of the bone plating assembly of FIG. 4.

FIG. 4 is a perspective view of bone plating assembly 200 according to another embodiment. Bone plating assembly 200 is similar to bone plating assembly 100, and therefore like elements are referred to with similar reference numerals within the 200-series. For instance, bone plating assembly 200 also includes a medial bone plate 210, a lateral bone plate 220 and a cross-connector 230. However, a collar 237 enclosing second fixation hole 234 does not have a ball nut joint in this embodiment. A cross-section of bone plating assembly 200 taken along line A-A of FIG. 4 is shown in FIG. 5. Similar to bone plating assembly 100, cross-connector 230 passes through medial cuneiform bone 142, an intermediate cuneiform bone 150, a lateral cuneiform bone 152 and cuboid bone 142.

Figure 6:
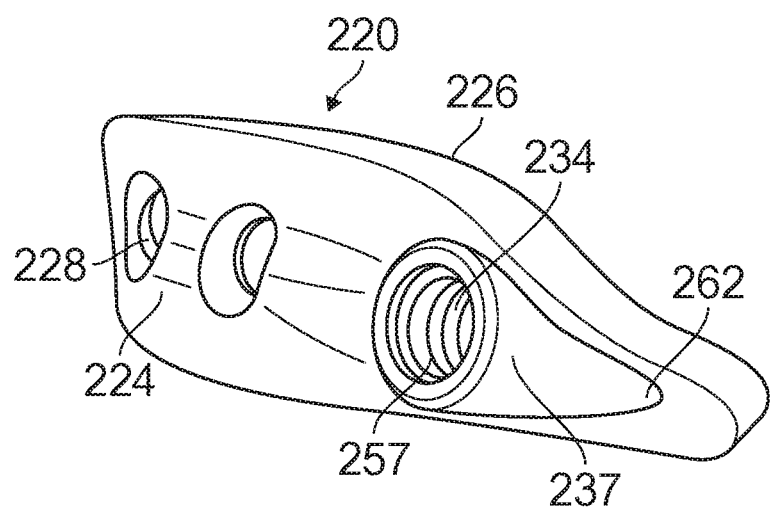
FIG. 6 is a side elevation view of a lateral bone plate of the bone plating assembly of FIG. 4.

FIG. 6 shows a side elevation view of lateral bone plate 220. Collar 237 has internal threading 257 configured to be secured with threading 238 of cross-connector 220 as best shown in FIG. 5. In this embodiment, lateral bone plate 220 is locked into position with respect to the cross-connector, when cross-connector 220 is threadingly secured to lateral bone plate 220. A tapered section 262 extends distally from the second fixation hole 234 and allows for improved contact between lateral bone plate 220 and cuboid bone 142 (not shown).

Figure 7A:
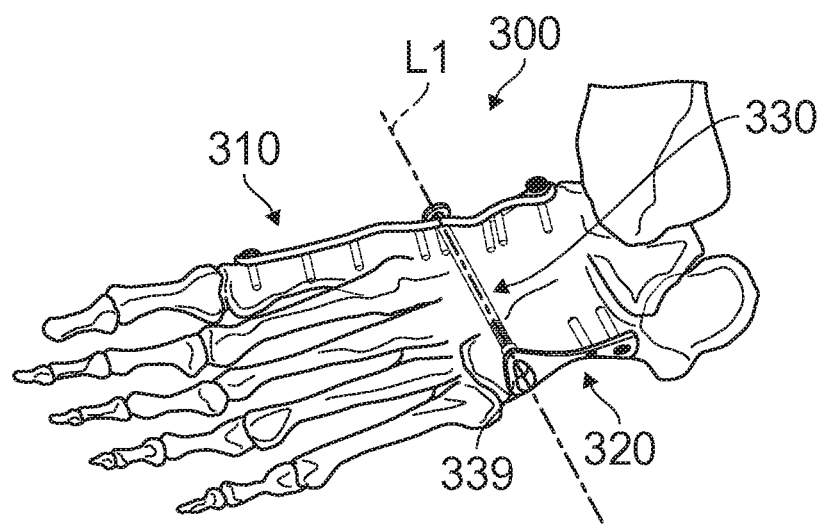
FIG. 7A is a perspective view of a bone plating assembly according to yet another embodiment of the present invention.
Figure 7B:
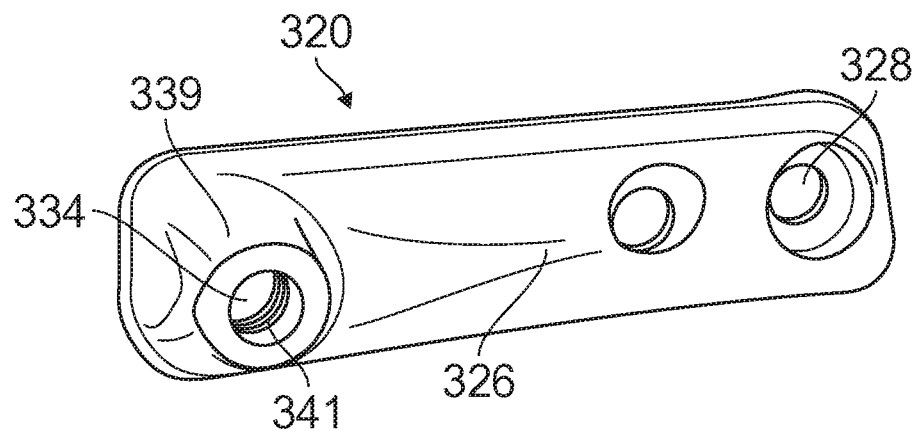
FIG. 7B is a side elevation view of a lateral bone plate of the bone plating assembly of FIG. 7A.

FIG. 7A is a perspective view of bone plating assembly 300 according to another embodiment. Bone plating assembly 300 is similar to bone plating assembly 200, and therefore like elements are referred to with similar reference numerals within the 300-series. For instance, bone plating assembly 300 also includes a medial bone plate 310, a lateral bone plate 320 and a cross-connector 330. However, a collar 339 enclosing second fixation hole 334 extends away from opposite second surface 326 of the lateral bone plate 320 in this embodiment. Consequently, second bone contacting surface 324 has a generally planar surface requiring less bone resection to place and secure lateral bone plate 320 on bone. Collar 339 is provided with internal threading 341 as best shown in side elevation view of lateral bone plate 320 in FIG. 7B. Threaded portion 338 of cross-connector 330 is configured to threadingly engage with internal threading 341 of lateral bone plate 320.

Bone screw holes and fixation holes may be threaded, non-threaded or made of deformable material as used in technologies such as the Smartlock System. Compatible bone screws including locking and nonlocking screws may be used to attach bone plates to bone. Bone plates may also be provided with other features including, but not limited to, compression slots, blind holes, suture anchors, and locking holes. Bone screw holes, fixation holes, and other features may be provided in any configuration across the bone plates. Preoperative planning may be used to determine optimum screw hole and fixation hole layout across bone plates. Bone plating assemblies of the present disclosure may also be used in conjunction with patient-specific plating systems including customized bone plates as disclosed in U.S. Provisional Application No. 62/482,422, the disclosure of which is hereby incorporated by reference herein.

Figure 8:
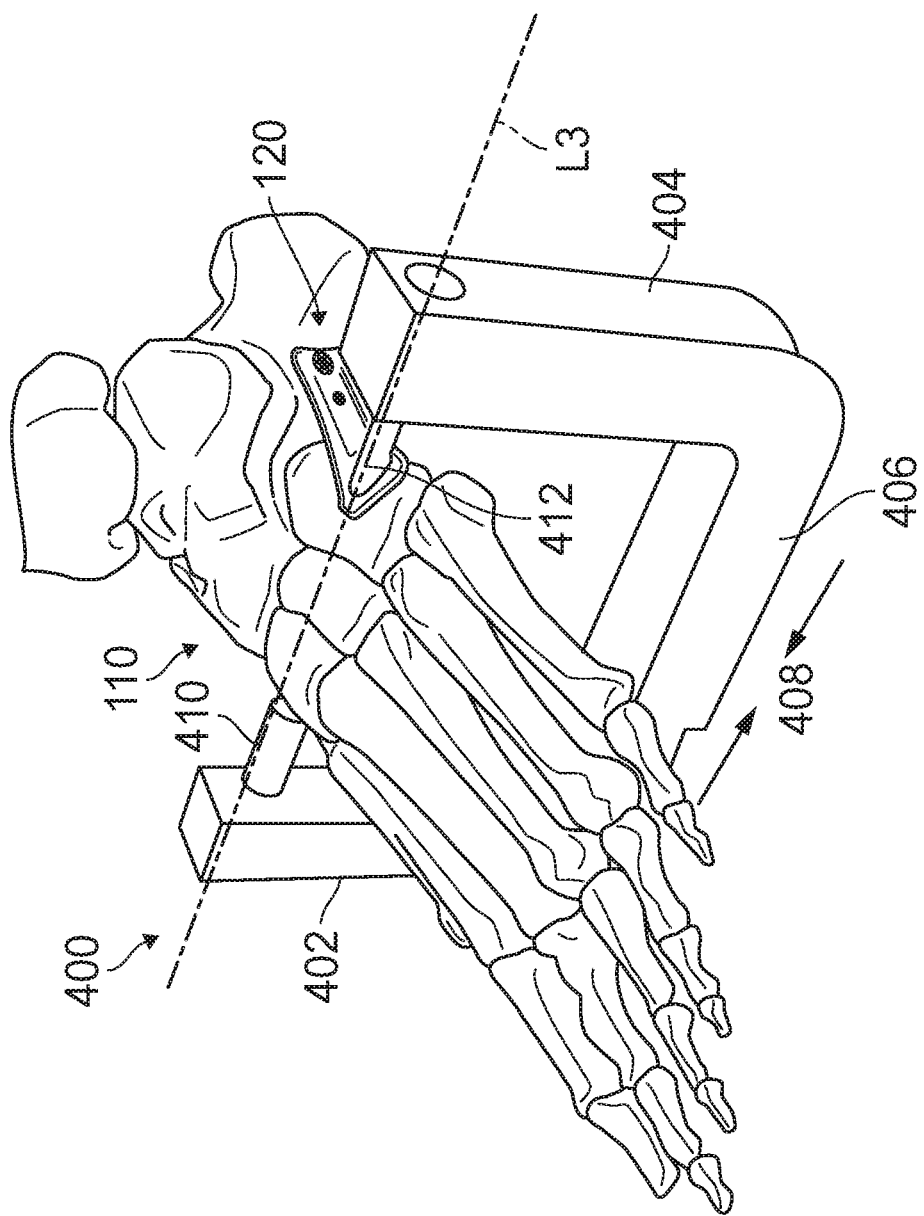
FIG. 8 is a perspective view of a targeter device according to an embodiment of the present invention.

FIG. 8 is a perspective view of a targeter device 400 according to an embodiment of the present invention. Targeter device 400 is shown in conjunction with bone plating assembly 100. Targeter device 400 is generally U-shaped and includes an expandable frame with a first leg 402 and a second leg 404. Second leg 404 is slidably coupled with first leg 402 at a distal end of targeter device 400. A spring 406 (not shown) is housed within the coupled region of the first and second leg such that the first and second leg are biased to move towards each other as indicated by directional arrows 408. A first column 410 and a second column 412 are attached to the proximal ends of first leg 402 and second leg 404 respectively. The distance between first column 410 and second column 412 may be adjusted by manually pulling the columns apart to compress spring 406, and therefore targeter device 400 can function as an expandable clamp for bone or bone assemblies of varying sizes. First column 410 and second column 412 are generally cylindrical with hollow interiors. The hollow interiors have a central targeter axis L3 which aligns with the central axis of the cross-connector L1 when first column 410 contacts medial bone plate 110 and second column 412 contacts lateral bone plate 120 as best shown in FIG. 8. Slidably coupled legs 402, 404 and spring bias 406 ensure that bone plates 110, 120 are securely held in place by functioning as a compression and distraction tool. Columns 410, 412 may now serve as drill guides to drill a cross-connector 130 hole. While a spring bias working in conjunction with slidable legs is shown in this embodiment, other embodiments may have other mechanisms to force columns 410, 412 towards each other.

Figure 9:
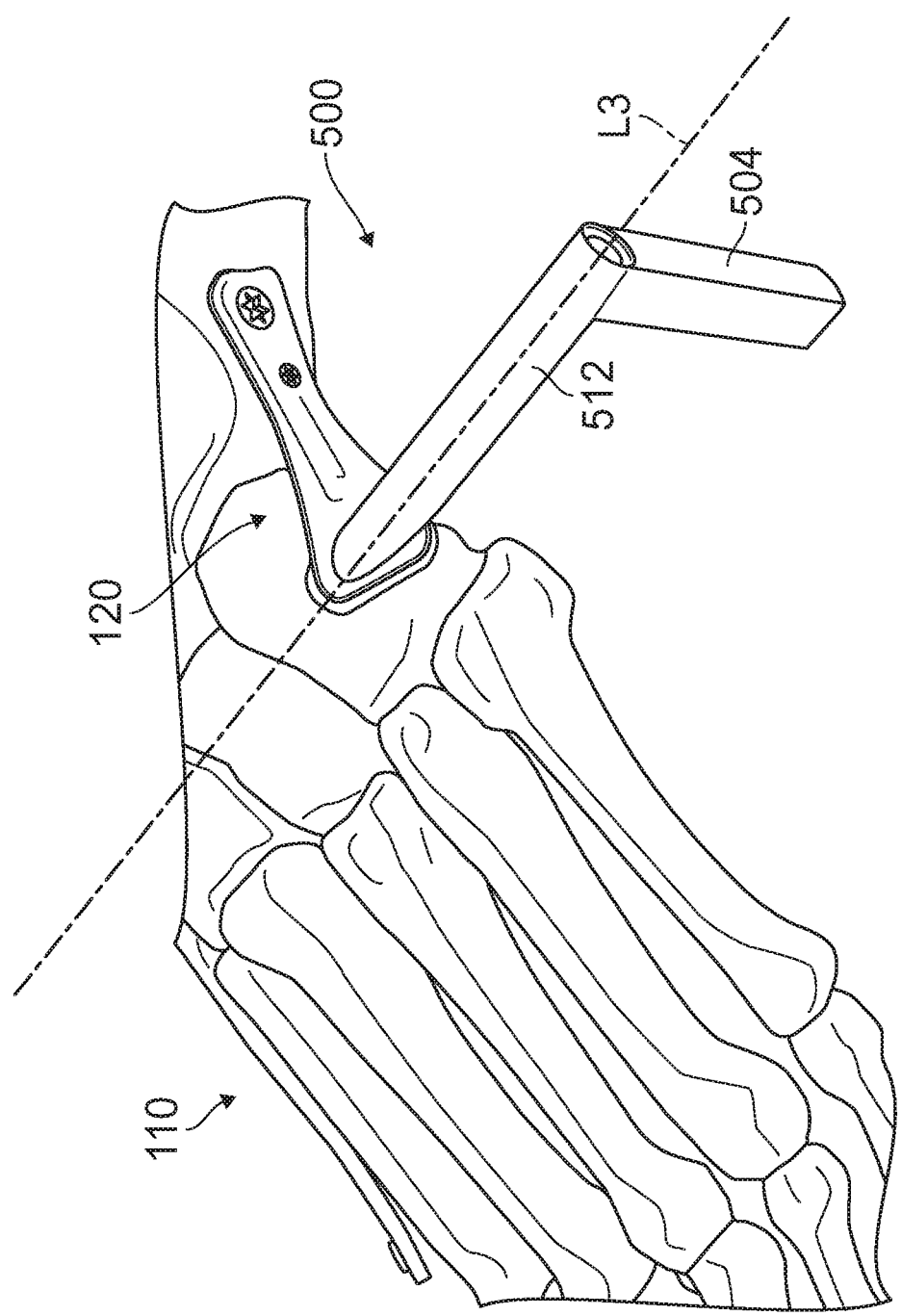
FIG. 9 is perspective view of a targeter device according to another embodiment of the present invention.

Referring now to FIG. 9, there is shown a perspective view of a targeter device 500 according to another embodiment. Targeter device 500 is similar to targeter device 400, and therefore like elements are referred to with similar reference numerals within the 500-series. First leg 502 and second leg 504 are not attached at a distal end in this embodiment. Consequently, placing first column 510 (not shown) on medial bone plate 110 and second column 512 on lateral bone plate 120 may be independently performed. This provides additional flexibility in placing targeter device 500 on target bones where accessibility is more constrained because columns 510, 512 may be individually placed on target site without requiring additional space for a jointed distal end.

Figure 10A:
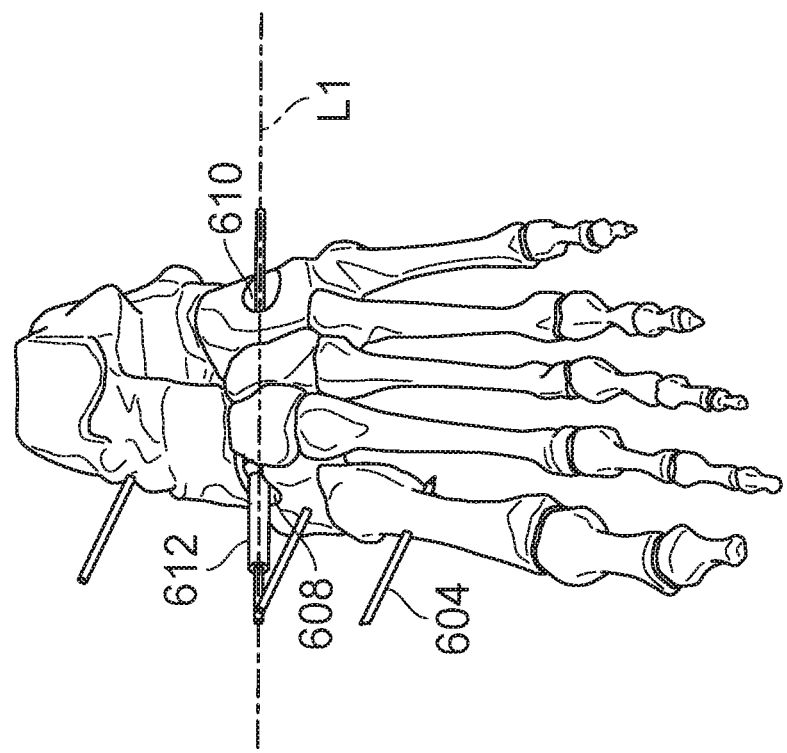
FIGS. 10A-10D are perspective view of a bone plating system showing the sequential steps of attaching the bone plating assembly of FIG. 1.
Figure 10B:
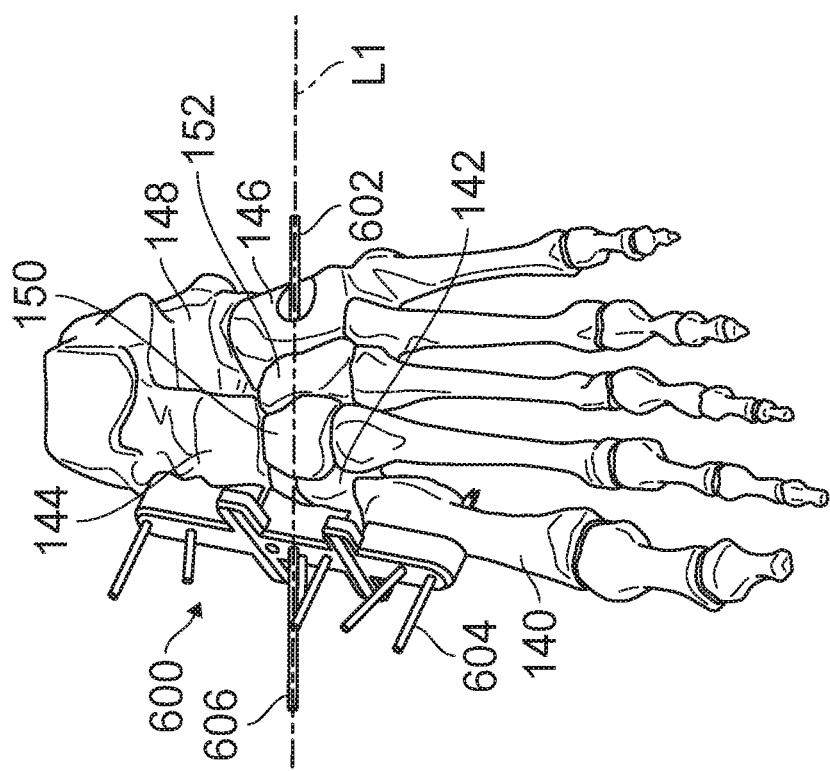
Figure 10C:
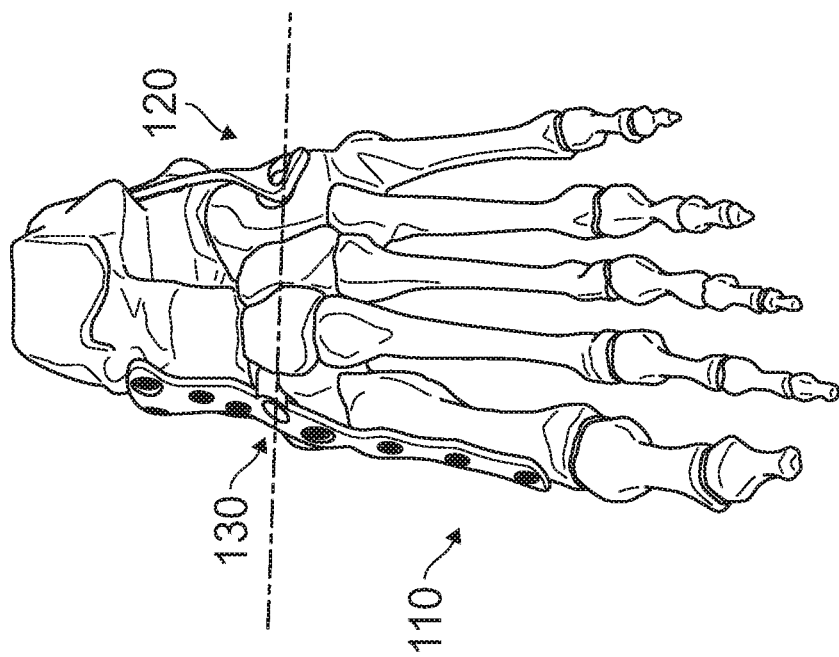
Figure 10D:
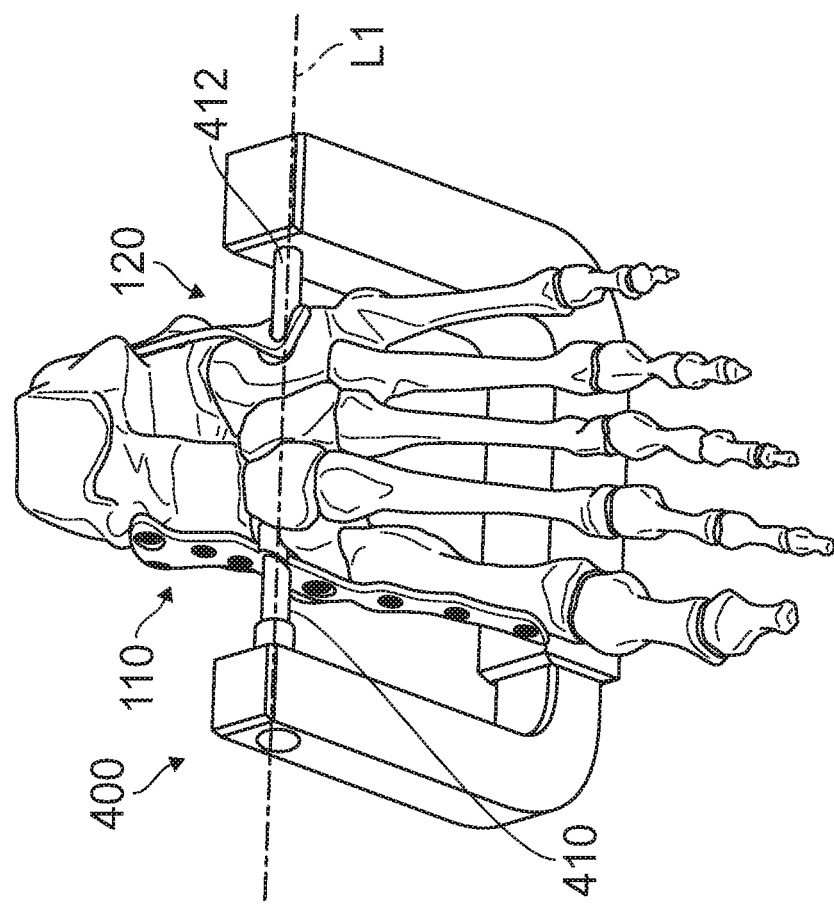

Another aspect of the present invention is a method is for attaching a bone plating assembly to multiple bones. Referring now to FIGS. 10A-10D, there is shown a method for implanting a bone plating assembly 100 during a surgical procedure such as Charcot arthropathy. A cutting guide 600 is placed on a medial side of a human foot across metatarsal bone 140, medial cuneiform bone 142, and navicular bone 144 as shown in FIG. 10A. Cutting guide 600 includes multiple slots for guidewire 604 attachment to bones 140, 142, 144. A central slot 606 having a central axis is aligned with the intended placement of cross-connector 130 by ensuring that this central axis is collinear with central axis of cross-connector L1. After securing cutting guide 600 by attaching guidewires 604 to bones 140, 142, 144, a hole is drilled along axis L1. A long guidewire 602 is placed in this hole. As best seen in FIG. 10A, a central axis of long guidewire 602 is collinear to axis L1. Cutting guide 600 is then removed along with some of the guidewires leaving behind at least a few guidewires 604. A first counterbore 608 on medial cuneiform bone 142 and a second counterbore 610 on cuboid bone 146 are resected as shown in FIG. 10B. A drill column 612 paced over long guidewire 602 ensures that counterbore holes 608,610 are aligned with axis L1.

Medial bone plate 110 is placed over bones 140, 142, 144, with the help of the remaining guidewires 604 such that first fixation hole 122 fits into counterbore 608. Similarly, lateral bone plate 120 is placed over bones 146, 148 with collar 136 being positioned in counterbore 610. Targeter device 400 is then used to secure and position bone plates 110, 120. First column 410 and second column 412 are retracted manually by pulling them apart to slide first leg 402 into second leg 404. Targeter device 400 is then placed on bone plates 110, 120, and aligned to ensure that targeter axis L3 is collinear with cross-connector axis L1. When the manual force to pull columns 410, 412 is removed, bias spring 406 forces columns towards each other to securely hold bone plates in place. Once proper alignment is confirmed, i.e., when axis L3 is collinear with L1, a few bone screws 118, 132 may be used to secure bone plates 110, 120. First column 410 and second column 412 may now be used as a telescopic drill guide to drill hole for cross-connector 130. Cross-connector 130 may then be fastened to medial bone plate 110 and lateral bone plate 120 to complete the implantation of bone plate assembly 100.

Prior to implantation of bone plate assembly 100, preoperative planning may be performed to customize and specifically design bone plates 110, 120 and cross-connector 130 for patient specific requirements. Patient-specific bone plating assembly 100 may then be implanted using universal tools such as cutting guide 600 and targeter device 400 which are compatible with bone plates of varying sizes.

While a bone plating assembly for a midfoot procedure such as Charcot arthropathy is described in these embodiments, bone plate assemblies, targeter device and cutting guide disclosed herein may be used in other surgical procedures. Various bone plate shapes and contours may be designed and fabricated to conform with specific bone requirements. The number of bones disposed between the plates may also be varied without departing from the scope of the present invention. Bone plates of the present invention may be made from any of, but not limited to, PEEK, polymers and titanium and/or titanium alloys, stainless steel, and cobalt chrome. Additive manufacturing techniques such as 3D printing may be used to fabricate bone plates. Cross-connector threaded portion may be limited to one end or two ends, or may be fully threaded.

Figure 11:
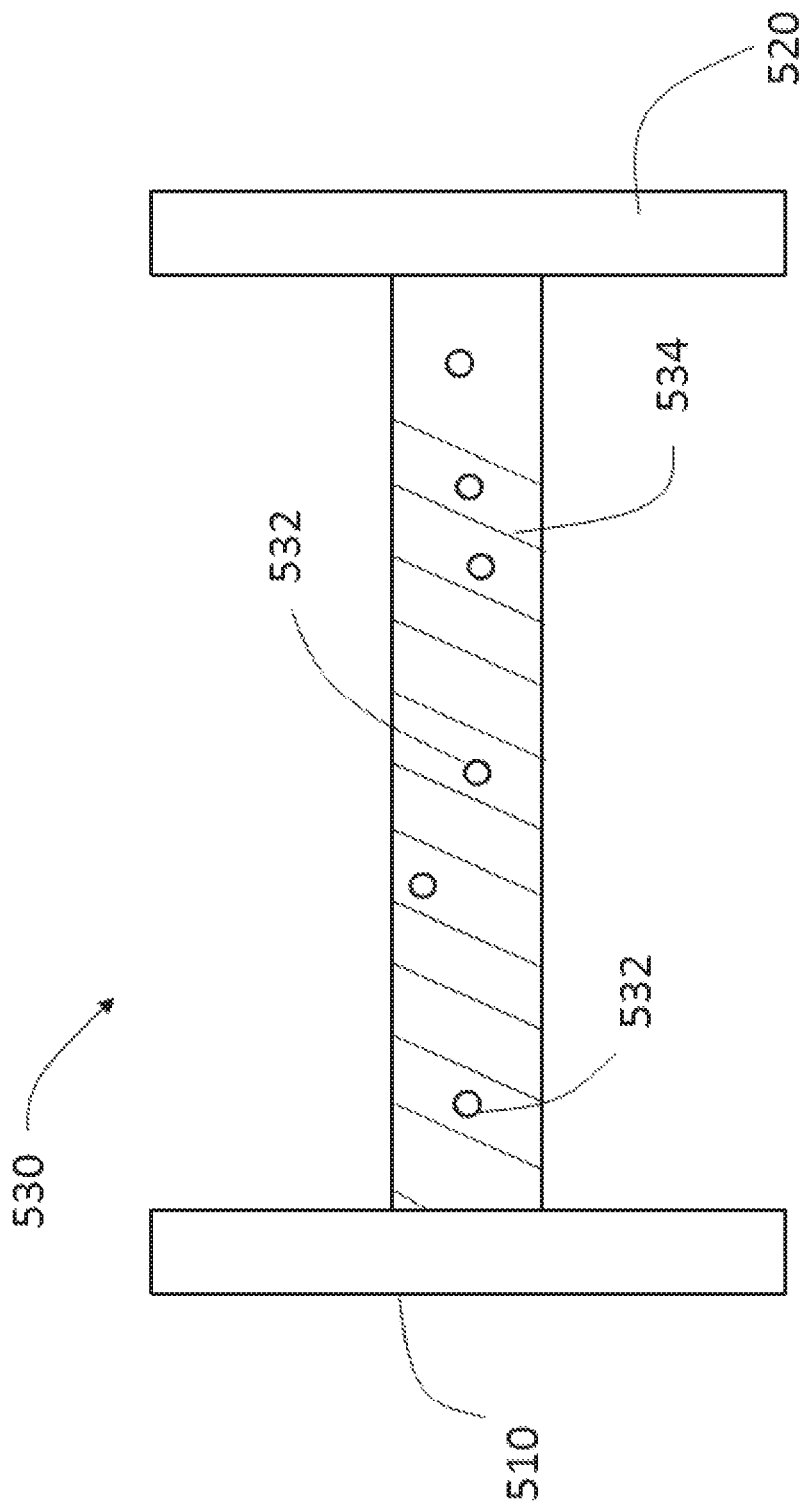
FIG. 11 is a side view of a bone screw according to another embodiment of the present invention.
Figure 12:
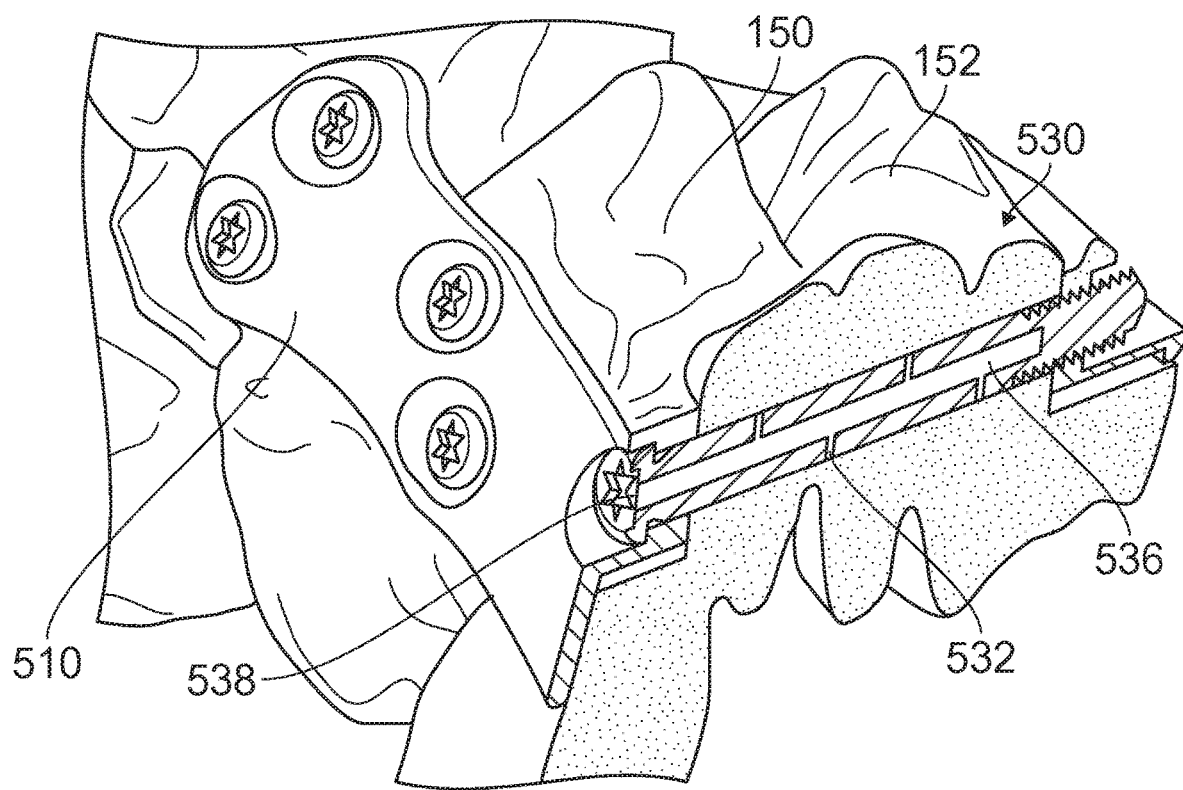
FIG. 12 is a perspective cross-sectional view along line L1 of the bone plating system of FIG. 10A with the bone screw of FIG. 11.

Referring now to FIGS. 11 and 12, there is shown a bone screw 530 according to an embodiment of the present invention. Medial plate 510 and lateral plate 520 of bone screw 530 is secured across intermediate cuneiform bone 150 and lateral cuneiform bone 152 respectively. Multiple biologic outlets 532 are disposed on the surface of bone screw 530. Each biologic outlet 532 is in fluid communication with an internal biologic channel 536 as best shown in FIG. 12. The location of biologic outlets 532 across bone screw 530 are configured for the precise dispersal of a biologic fluid at the desired locations. Once the bone screw is secured to the plates and the bone, the biologic fluid can be introduced through an inlet 538. The biologic fluid fills channel 536 and flows through outlets 532 to the desired locations. The biologic fluid within channel 536 reinforces and strengthens bone screw 530. As best shown in FIG. 11, outlets 532 can be located in threaded portion 525 of bone screw 530 between threads 534 or in an unthreaded portion of the bone screw. The threaded portion can include single or double start threads, for example, or forward or reverse threading depending on the bone screw insertion area and bone type.

FIG. 13 shows a bone screw 630 according to another embodiment of the present invention. Bone screw 630 includes three biologic outlets 632a, 632b and 632c located between screw threads 634 across the bone screw. Bone screw 630 may include more or less than three biological outlets 632 in other embodiments. Biological outlets 632 each include a longitudinal axis which may be parallel or transverse to one another. Each biological outlet 632 has a diameter D1. Respective diameters D1 of biological outlets 632 may be less than, equal to or greater than one another. Biological outlets 632 generally have a constant diameter from their respective inlets and outlets but may have a varying diameter forming a conical shape for example. In such embodiments, biological outlets 632 may have a greater diameter at the inlet than at its outlet for example. In other embodiments, biological outlets 632 may include an inner ledge such that it includes first and second cylindrical portions having respective larger and smaller diameters. In yet other embodiments, biological outlets 632 may include a tapered portion intermediate first and second cylindrical portions of increasing or decreasing diameters for example. Bone screw 630 includes an internal channel (not shown) configured to receive an insert to control the opening and closing of the biologic outlets. For example, a first insert 635a as shown in FIG. 14A includes an opening 632c'. When first insert 635a is introduced into bone screw 630a as shown in FIG. 14B, outlets 632a and 632b are closed leaving only outlet 632c in fluid communication with an internal channel of the insert.

FIG. 15A shows a second insert 635b having openings 632a' and 632b' corresponding to outlets 632a and 632b. When second insert 635b is inserted into bone screw 630b only outlets 632a and 632b are in fluid communication with an internal channel of the insert as best shown in FIG. 15B. Bone screws in other embodiments can have various numbers of biologic outlets disposed along the bone screws and can be paired with corresponding inserts to control opening and closing of the biologic outlets as desired. Biologic fluids can include bone cements such as polymethyl methacrylate ("PMMA"), methyl methacrylate ("MMA"), etc., to anchor joints and fractured bones. While a bone screw bridging two plates is described here, other embodiments may have include bone screws with biologic outlets secured in conjunction with one or more bone plates. Bone screws with biologic outlets described here can also be used with other implants in other embodiments of the present disclosure.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A bone plating system comprising:
   first and second bone plates configured to be in contact with respective first and second bones;
   a cross-connector having a first end and an opposite second end, the cross-connector extending along a longitudinal axis from the first bone plate to the second bone plate;
   a cutting guide having an elongate body with a bone contacting surface configured to be placed on one of the first and second bones to define the longitudinal axis; and
   a targeter device having a drill guide to align the cross-connector with the first and second bone plates along the longitudinal axis.

2. The bone plating system of claim 1, further comprising an insert housed within one of the first and second bone plates, wherein the second end of the cross-connector engages with the insert to secure the cross-connector about the longitudinal axis.

3. The bone plating system of claim 2, wherein one of the first and second bone plates with the insert is moveable about at least one axis extending through said bone plate when said bone plate is secured to the cross-connector.

4. The bone plating system of claim 2, wherein the insert is any of a ball joint nut, pivot nut and flexible nut.

5. The bone plating system of claim 1, wherein the cross-connector includes a first threaded portion to engage with one of the first and second bone plates.

6. The bone plating system of claim 1, wherein an outer surface of the second bone plate includes a collar portion extending outwardly therefrom, the second end of the cross-connector being at least partially disposed within the collar when the cross-connector is secured to the first and second bone plates.

7. The bone plating system of claim 1, wherein a bone contacting surface of the second bone plate includes a collar portion extending outwardly thereofrom, the second end of the cross-connector being at least partially disposed within the collar when the cross-connector is secured to the first and second bone plates.

8. The bone plating system of claim 1, wherein the first and second bone plates each have at least one fixation hole.

9. The bone plating system of claim 8, wherein the at least one fixation hole is a compression slot.

10. The bone plating system of claim 1, wherein the first bone plate is configured to contact at least one of a metatarsal bone, a cuneiform bone, a navicular bone and a talus bone and the second bone plate is configured to contacts at least one of a cuboid bone and a calcaneus bone.

11. The bone plating system of claim 1, wherein the first and second bone plates are preoperatively planned to match an outer surface of the respective first and second bones and to secure the cross-connector along the longitudinal axis.

12. The bone plating system of claim 1, wherein the cutting guide has a slot extending through the elongate body, the slot having a central axis collinear with the longitudinal axis.

13. The bone plating system of claim 1, the targeter device further comprising a frame having a first arm and a second arm, a through hole through each of the first and second arms defining a targeter axis extending from the first arm to the second arm, the targeter axis being collinear with the longitudinal axis when the first and second arms are engaged with the respective first and second bones.

14. The bone plating system of claim 13, wherein at least one of the first arm and the second arm is a spring loaded retractable arm such that the targeter device is retractable along the targeter axis.

15. The bone plating system of claim 14, wherein the first and second arms couple the targeter device to the first and second bone plates such that the targeter axis is collinear with the longitudinal axis.

16. The bone plating system of claim 1, wherein the cross-connector is configured to extend through a third bone disposed between the first and second bones to secure the first, second and third bones with the first and second bone plates.

17. The bone plating system of claim 1, wherein the cross-connector includes a channel in fluid communication with one or more outlets disposed on an outer surface of the cross-connector, the channel having an inlet to receive a biologic fluid.

* * * * *